United States Patent [19]

Clough et al.

[11] 4,351,006

[45] Sep. 21, 1982

[54] METHOD OF AND APPARATUS FOR STORING DATA SIGNALS

[75] Inventors: Peter Clough, Warrington, England; Donald C. B. Walker, deceased, late of Lymm, England, by Eileen F. Walker, Administratrix

[73] Assignee: United Kingdom Atomic Energy Authority, London, England

[21] Appl. No.: 127,911

[22] Filed: Mar. 6, 1980

[30] Foreign Application Priority Data

Mar. 19, 1979 [GB] United Kingdom ................. 7909588

[51] Int. Cl.³ ...................... H04N 5/79; H04N 5/795; G01D 5/12
[52] U.S. Cl. ........................................ 360/9; 358/127; 360/6; 360/37
[58] Field of Search ....................................... 360/8–10, 360/32, 33, 5–6, 37; 358/127–132; 73/584, 588, 596–600, 602–631; 340/3 F

[56] References Cited

U.S. PATENT DOCUMENTS

| | | | |
|---|---|---|---|
| 3,036,151 | 5/1962 | Mitchell et al. | 358/256 |
| 3,142,032 | 7/1964 | Jones | 360/9 |
| 3,549,799 | 12/1970 | Sander | 360/9 |
| 3,610,820 | 10/1971 | Lund | 360/33 |
| 3,789,137 | 1/1974 | Newell | 360/8 |
| 4,111,055 | 9/1978 | Skidmore | 73/620 |

OTHER PUBLICATIONS

Matzuk et al, Novel Ultrasonic Scanner Featuring Servo Controlled Transducers Displacing a Sector Image, Ultrasonics 7/78, pp. 171–178.
Daniels, Wireless World Teletext Decoder, Wireless World, 2/76, pp. 47–51.
Daniels, Wireless World Teletext Decoder, Wireless World, 4/76, pp. 64–68.
Kreps, Formation of TV Signal in Flaw Detector With Automatic Mechanical Scanning on the Basis of Digital Memory, Soviet J. of Nondestructive Testing, vol. 15, No. 6, 6/79, pp. 543–546.

Primary Examiner—Raymond F. Cardillo, Jr.
Attorney, Agent, or Firm—William R. Hinds

[57] ABSTRACT

A method and apparatus for storing data signals, which data signals comprise radio frequency ultrasonic signals from an ultrasonic transducer and positional signals from a source associated with the transducer, wherein the signals are converted into a format in which they are compatible with a video recorder and stored on video recording magnetic tape for reproduction as required. Because the data signals are recorded live rather than in the form of a cathode ray oscilloscope display, they can be rectified as necessary. Positional coordinates of the transducer may be stored, and scans at varying thresholds can be reproduced. Position and ultrasonic data signals are interleaved on the video recording magnetic tape. Apparatus for performing the method includes a video recording device having a rotatable head and interface units for converting the radio frequency signals into television format and for decoding the signals for reproduction.

7 Claims, 7 Drawing Figures

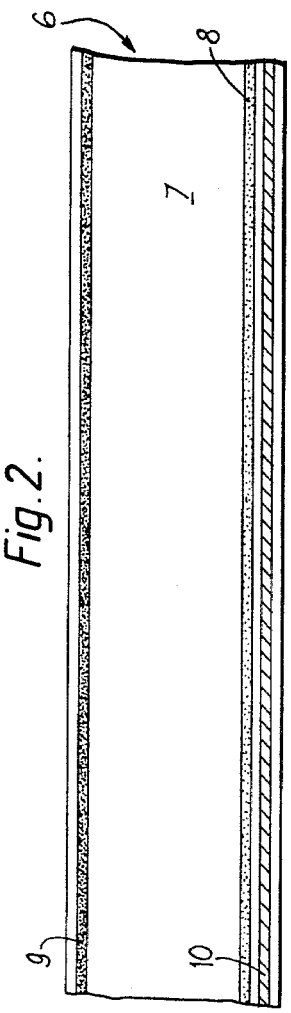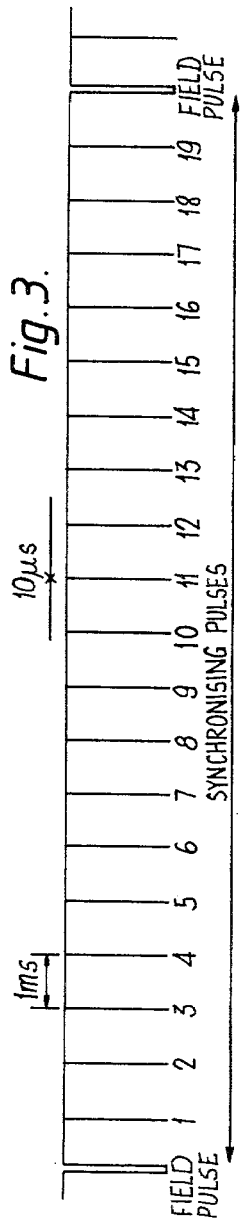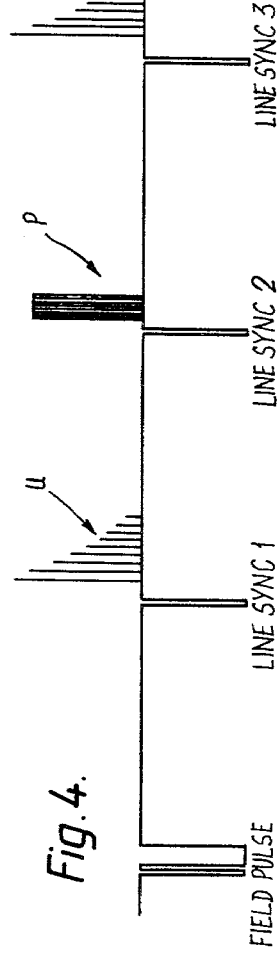

METHOD OF AND APPARATUS FOR STORING DATA SIGNALS

BACKGROUND OF THE INVENTION

This invention relates to methods of, and apparatus for, storing data signals, which data signals comprise radio frequency ultrasonic signals from an ultrasonic transducer and positional signals from a source associated with the transducer for subsequent reproduction.

Ultrasonic techniques and apparatus are employed in non-destructive testing, as is well known, the data signals received from ultrasonic transducers, being analogous to defects in the work piece being examined, may be displayed on a cathode ray oscilloscope or digitised and stored in a computer system. For storage of the signals whereby results of the examination can be pictorially re-displayed, it is known to record the pictorial representation of the oscilloscope display but unfortunately such recorded signals, which may have been processed before the original display, are dead precluding any further processing and are reproduced only with very poor resolution. Direct recording of the signals on magnetic tape is not practised because the high frequencies involved require excessive tape speeds and therefore large amounts of tape.

An object of the present invention is to provide a method of, and apparatus for, storing data signals from the ultrasonic transducers so that the signals can be reproduced in their original form and electronically processed where required.

SUMMARY OF THE INVENTION

According to one aspect of the present invention, a method of storing data signals from an ultrasonic transducer whereby signals transmitted by the ultrasonic transducer are stored on tape for subsequent reproduction is characterised in that the radio frequency signals transmitted from the ultrasonic transducer are converted into television format prior to recording so that they may be stored on video recording magnetic tape. The band width of radio frequency signals is similar to that used for recording television pictures so that by converting them to television wave form they can be stored on video recording magnetic tape and subsequently reproduced in their original live form, rectified or unrectified, to permit subsequent signal processing.

Pulsed signals corresponding to positional coordinates of the transducer are generated by encoders associated with the transducer, and converted into television wave form and stored on the tape for synchronisation of the tape with signal reproducing apparatus so that B-scans, for example, at varying thresholds (i.e. datum reference levels) can be reproduced. The ultrasonic information may be interleaved with transducer positional information on the video recording magnetic tape.

According to another aspect of the present invention, an apparatus for storing data signals from an ultrasonic transducer and position signals from a source associated with the transducer and comprising recording apparatus for storing and reproducing radio frequency signals transmitted from an ultrasonic transducer is characterised in that a first interface unit converts the signals into television format for storage on video recording magnetic tape, and in that a second interface unit decodes the signals into their original form on reproduction. The first interface unit may comprise means for interleaving information of differing types so that it can be stored on the same tape. The second interface means may comprise means for decoding the information of differing types.

Preferably, the apparatus comprises means for converting pulsed signals corresponding to positional coordinates of the transducer into television format and for storing the converted signals on the tapes for subsequent reproduction. Ultrasonic and positional data may be interleaved on the tape. The apparatus may include a second rotatable video head to enable video play-back during the record mode of operation.

DESCRIPTION OF THE DRAWINGS

A method of, and apparatus for, storing data signals in accordance with the invention is now described by way of example only with reference to the accompanying drawings in which:

FIG. 2 is a diagram of a specimen of video recording tape,

FIG. 3 shows part of a wave form formed in the apparatus of FIG. 1,

FIG. 4 is a similar view to FIG. 3 but of a different wave form,

DESCRIPTION OF THE PREFERRED EMBODIMENT

Figure 1A:
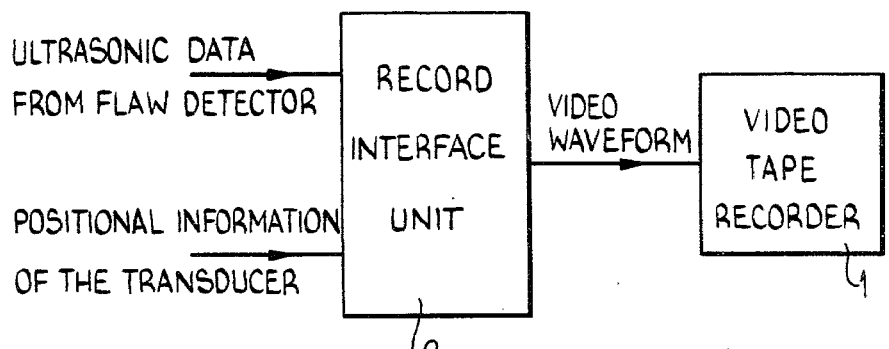
FIGS. 1a and 1b show a recording system and a replay system respectively.
Figure 1B:
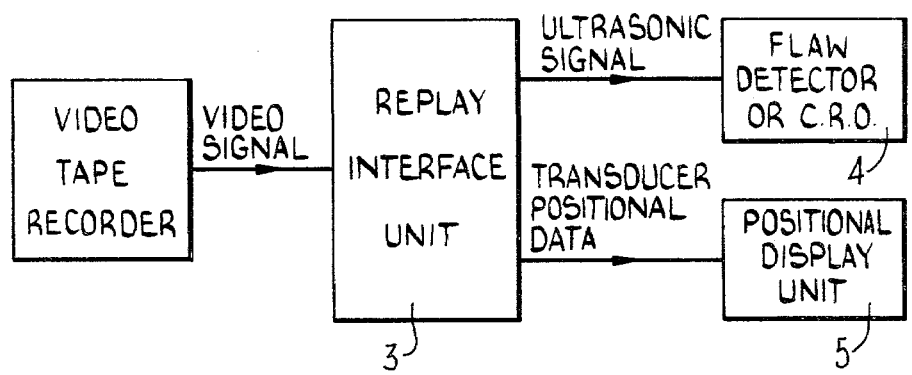

The apparatus shown schematically in FIGS. 1a and 1b comprises a video tape recorder 1 having a rotatable head and operable within a band width of 25 Hertz to 5 Mega Hertz. A recording interface unit 2 shown in FIG. 1a converts signals from an ultrasonic transducer into television format. These signals may include both ultrasonic data and transducer positional data. The television format signals may be stored on video recording magnetic tape.

A replay interface unit 3 shown in FIG. 1b decodes the signals into the original form. Output ultrasonic signals from the replay interface unit are fed to a flaw detecting cathode ray oscilloscope 4 whilst the transducer positional signals are fed to a positional display unit 5. Band width of the radio frequency signals from the transducer is similar to that employed for recording television signals, so that the signals can readily be converted into television wave form providing a suitable tape speed relative to the record-replay head can be achieved. Rotation of the head serves to increase the relative velocity between the tape and the head when a practical tape speed is used. Therefore, economic use of tape is achieved in comparison with a fixed head machine. In order to maintain the receiver in step with the transmitter field synchronising signals similar to those used in television systems are needed.

Reference is now made to FIG. 2, wherein a specimen piece of tape is indicated by 6. Ultrasonic data and positional information from flaw detecting transducers are recorded on the main video part of the tape 6, which part is indicated by 7. Synchronisation signals are recorded on a control track 8. Audio tracks 9 and 10 are also shown on the tape, but these are redundant in the present application. In a television system, there are normally 525 line synchronising pulses and 2 field synchronising pulses for each frame, the frame repetition frequency being 30 Hertz. This line repetition rate is too fast for recording ultrasonic data from thick specimens.

For a recording system for ultrasonic data, a simplified simulated field pulse 11, which is shown in FIG. 3 to which reference is now directed, is produced to operate the servo mechanisms which control the speed of the head. Between successive field pulses there are 19 modified line synchronising pulses 12 which are of about 10 micro seconds duration and are 1 millisecond apart. This system of synchronisation permits a repetition rate of nine hundred and fifty pulses per second. As well as recording the ultrasonic information, it is necessary to record the positional information of the probe if B-scan pictures are to be reconstituted. Therefore, the ultrasonic data is interleaved with the positional information. With reference to FIG. 3, it can be seen that the ultrasonic data is insertable adjacent to odd numbered modified line synchronisation pulses whereas positional information in digital form is associated with the even numbered modified line synchronisation pulses. Consequently, the system is capable of recording five hundred ultrasonic pulses per second together with four hundred and fifty pieces of positional data per second. The recorded wave form connected with the information can be clearly seen in FIG. 4 to which reference is now directed, the same reference numerals as FIG. 3 being used for like parts. In FIG. 4, ultrasonic data is indicated by U and positional information by P. From FIG. 4, there can be seen the difference between, on the one hand, ultrasonic signals which are amplitude variable radio frequency signals and, on the other hand, positional data signals which are digital signals such as BCD signals (wherein the presence or absence of a signal at a certain spacing indicates 1 or 0). In passing, it is to be noted that the ultrasonic data recorded on the tape in FIG. 4 is that which would arise from an unflawed material, since the magnitude of signal becomes less at each reflection.

It is to be understood, that the field synchronising signals activate the video recorder servo mechanism which controls the speed of the rotating head of the recorder to ensure that the head maintains a fixed relationship with the video signal. The recorder 1 is a high performance helical scan device which allows sufficient time between successive modified line synchronising pulses for the ultrasonic data to be recorded and still permits the video servo mechanism to function correctly in response to the field synchronising pulses so as not to impair the performance of the recorder. The recorder also has a second video head to allow video play-back during the recording mode of operation thereby enabling the quality of the recording to be checked during said recording mode.

Figure 5:
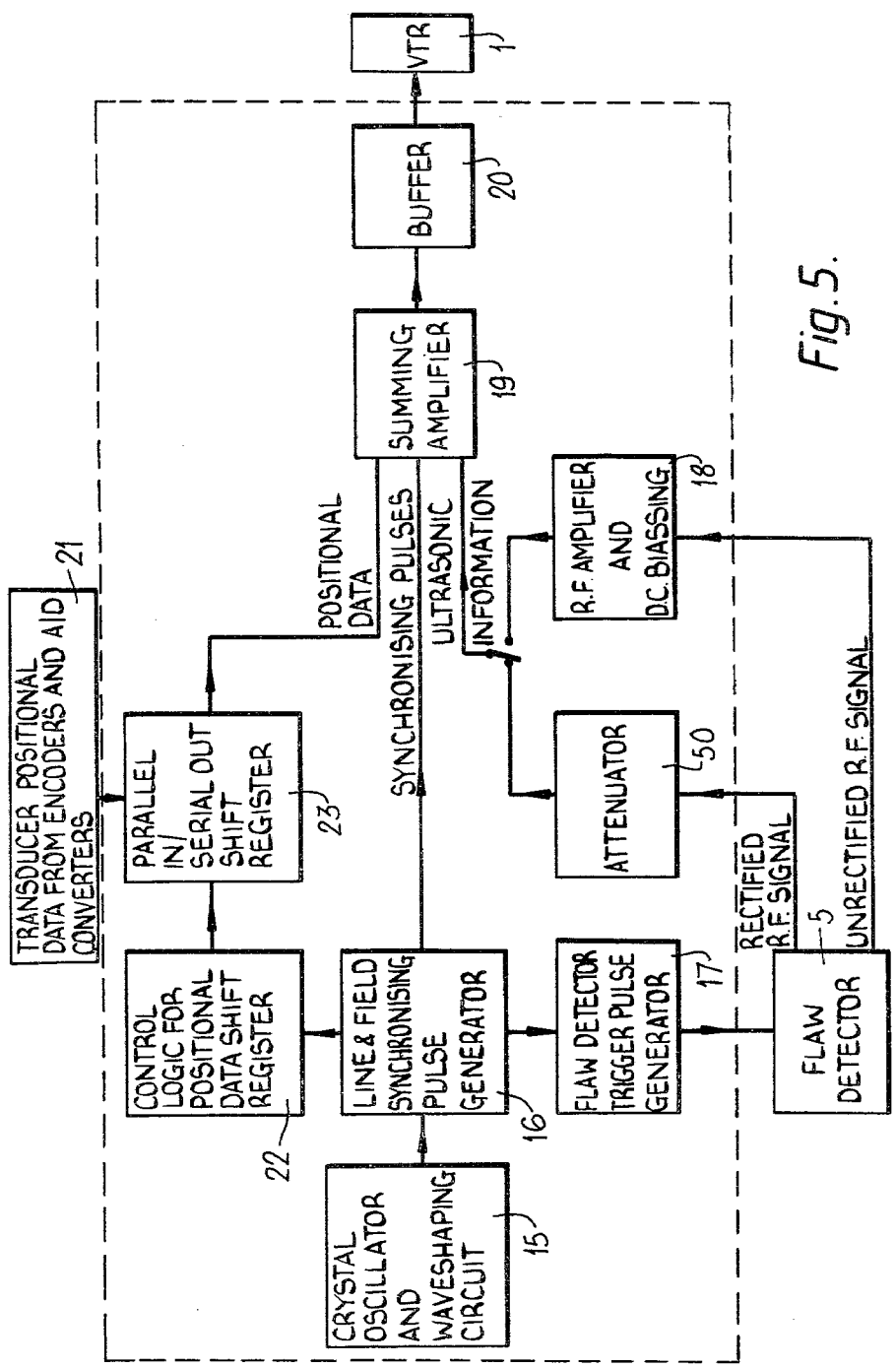
FIG. 5 is a simplified block diagram of a record interface unit.

Reference is now directed to FIG. 5 which is a simplified block diagram of the record interface unit 2, and wherein like reference numerals to preceding Figures are used for like parts. A crystal oscillator and wave shaping circuit 15 produce a square wave signal at a frequency, for example of 1.25 Mega Hertz. This is a basic clock frequency which is divided down by TTL counters and used to trigger a line and field synchronising pulse generator 16, which generator 16 comprises a series of mono stable multi vibrators which are able to produce field and line synchronising pulses, at its simplest, the series being one monostable circuit for field pulses and one for modified line pulses, but for example two monostables being required to form a field pulse similar to that shown in FIG. 4.

Signals from the generator 16 are used to provide timing pulses for trigger pulse circuit 17 associated with the flaw detector 5. The flaw detector 5 is triggered immediately after alternate odd numbered line pulses. This would produce a pulse repetition rate at the flaw detector of 500 Hertz. Provision is made to reduce this by a factor of 2 in situations where the higher pulse repetition rate would not allow satisfactory attenuation of signals being reflected in a specimen under examination between triggerings. Thus, the pulse repetition rate is reduced to 250 Hertz in such situations so that the flaw detector is triggerd solely after modified line synchronising pulses 1, 5, 9, 13 and 7 (see FIG. 4).

The ultrasonic radio frequency signal from the flaw detector can be recorded in either rectified or unrectified form. The rectified signal passes through an attenuator 50. The unrectified signal is superimposed on a direct current bias by a circuit 18 prior to feeding into the recorder 1 through a summing amplifier 19 and a buffer amplifier 20. The ultrasonic information is inserted onto the wave form from the synchronising generator 16 by the feeding of the signals through the summing amplifier 19.

Positional information, which may be in digital form from encoders associated with the ultrasonic transducers or may be converted to digital form by analogue to digital converters (all of which signal sources are indicated by 21), is interleaved with the ultrasonic data and is inserted adjacent to even numbered line synchronising pulses by means of a control logic circuit 22 for positional data shift register 23, which is a parallel in/-serial out shift register. Control signals from the synchronising generator 16 are used to provide timing pulses for logic circuits which control the entry of the positional data, the line frequency being a divided frequency from the clock. Therefore, it will be understood that the digital information is fed in parallel form into the shift registers 23. Control logic, which is simply an arrangement of logic gates, enables the information to be fed out of the shift registers in serial format after the occurrence of even numbered line pulses. The positional information then passes into the summing amplifier 19, wherein it is added to the synchronising signal.

A complete composite video wave form is obtained when the ultrasonic information and the positional data are added onto the synchronising signal. This composite video wave form is then passed through the buffer amplifier 20 which provides the necessary matching output impedance for feeding the signal into the video tape recorder.

Figure 6:
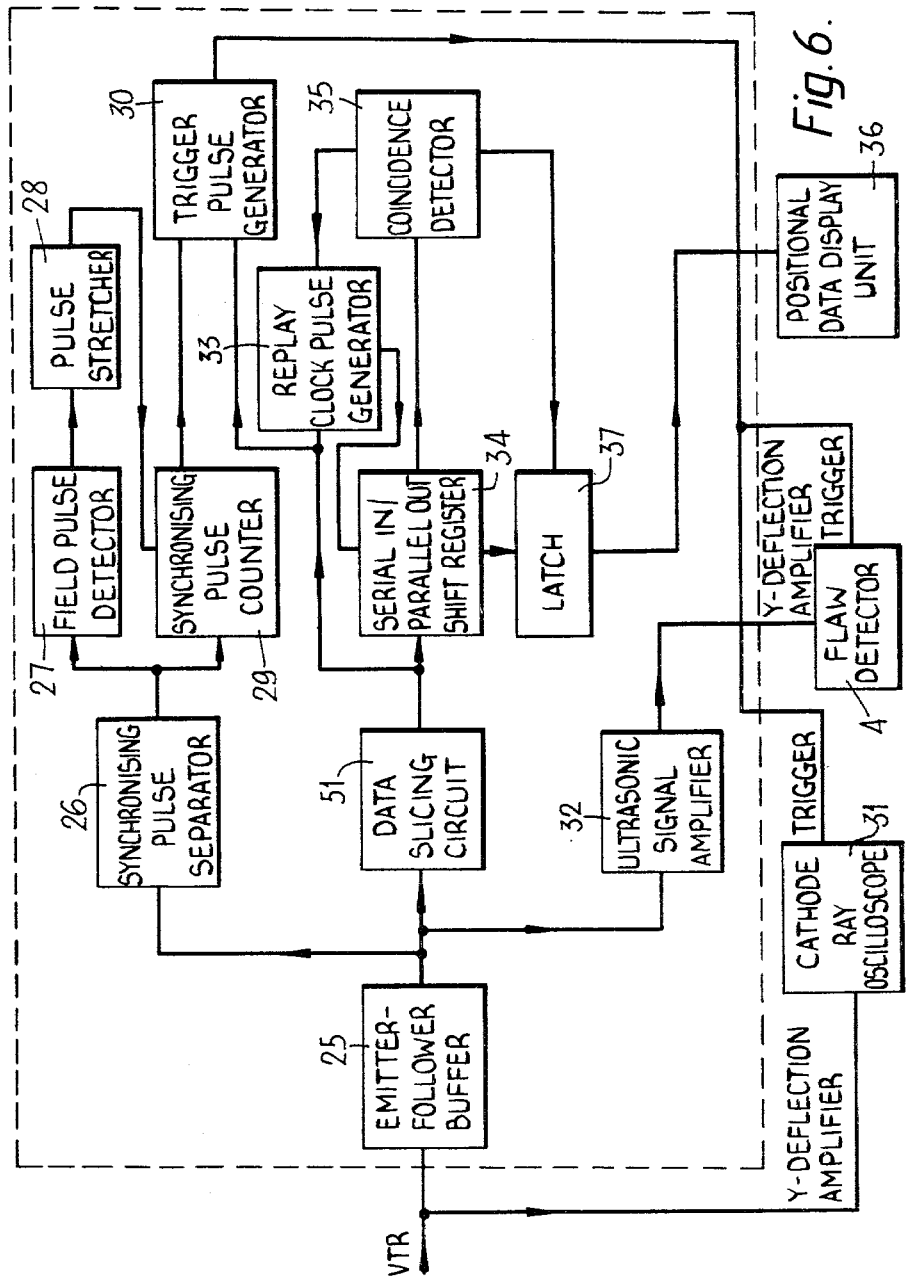
FIG. 6 is a simplified block diagram of a replay interface unit.

Reference is now directed to FIG. 6, which is a simplified block diagram of the replay interface unit 3. The replay interface unit 3 performs the following basic functions:

(a) Separation of the mixed synchronising pulses from the ultrasonic and positional data.

(b) Triggering of the oscilloscope and the flaw detector at the appropriate time to display the ultrasonic information.

(c) Amplification of the rectified ultrasonic signals to a level suitable for feeding into the Y-deflection amplifiers of the flaw detector.

(d) Slicing the positional data to enable it to be decoded and displayed.

The composite video signal enters an emitter-follower buffer circuit 25 which provides a low impedance source. The mixed synchronising or control signal is then separated from the composite signal by a synchronising pulse separater 26. As has been explained, the control signal or synchronising signal provides a simplified field synchronising signal which is needed to control the speed of the tape recorder head. The field pulse is then detected in a circuit 27 and stretched by a circuit 28 to provide a necessary blanking period during head cross-over noise. This noise results during replay when the head is between the end of one scan and the beginning of the next scan and is an inherent function of the operation of the recorder. The blanking period extends until after the appearance of the first modified line synchronisation pulse so that data associated with this pulse is lost. Hence, the first batch of ultrasonic information to be detected on replay is that associated with modified line synchronisation No. 3. Each modified line synchronisation pulse is counted in a counter 29 and a pulse is generated by a generator 30 to trigger an oscilloscope 31 and the flaw detector 4. This allows the ultrasonic information to be displayed on the oscilloscope, which has its own amplifier and timebase. However, to reconstitute a so-called B-scan it is required to display the ultrasonic information on a flaw detector, which does not have a suitable internal amplifier. The radio frequency signals which are replayed from the tape recorder are therefore amplified by an amplifier 32 before being applied to the Y-deflection plates of the flaw detector. Naturally, the oscilloscope or flaw detector, as the case may be, does not display positional data because it is not triggered at this time.

The replay interface unit also decodes the positional data. During the initial recording process 2 pre-set patterns are fed onto the tape which are used to operate the replay circuits. The first pattern is used to synchronise a replay clock pulse generator 33 to the speed at which the data is being replayed. The replay clock moves the positional data, which is in serial format, through a series of shift registers 34. The second pre-set pattern is recognised at a coincidence detector 35 (for example a NAND gate) which stops the replay clock and moves the data out of the shift register in parallel form to the display unit 36 by way of a latch 37. A data slicing circuit 51 for slicing synchronising from data signals is arranged between the buffer 25 and register 34.

From the above description, it can be seen that the invention provides an apparatus which is capable of recording rectified or unrectified ultrasonic signals directly in analogue form using a video tape recorder. The apparatus is capable of recording simultaneously the positional co-ordinates of the transducer thereby permitting B-scan pictures to be reconstructed from the replayed signals. This is possible because of the interleaving of ultrasonic data and the positional information on the video magnetic tape. The interleaving is achieved according to a specified pattern, which pattern (constituted by a series of line synchronisation pulses) controls the head of the recorder.

We claim:

1. A method of storing data signals from an ultrasonic transducer for subsequent reproduction, comprising receiving radio frequency data signals transmitted from the ultrasonic transducer and positional data signals from a source associated with the transducer and converting said radio frequency data signals and said positional data signals into a format in which they can be recorded on tape by a video recorder which has a head servo driven by field synchronising pulses, said converting being effected by generating modified line synchronising pulses, selecting a first group of the modified line synchronising pulses and transmitting said radio frequency data signals to the video recorder when said first group of modified line synchronising pulses occurs, and selecting a second different group of the modified line synchronising pulses interleaved wtih said first group of modified line synchronising pulses and transmitting said positional data signals to the video recorder when said second group of modified line synchronising pulses occurs, whereby said radio frequency data signals and said positional data signals are interleaved on the tape.

2. A method as claimed in claim 1, in which the first group of pulses are selected with a temporal spacing which is adjustable to allow a separation which is great enough to minimize interference between successive batches of radio frequency signals.

3. Apparatus for storing radio frequency data signals transmitted from an ultrasonic transducer and positional data signals from a source associated with the transducer, the apparatus comprising a video recorder which has a head servo driven by field synchronising pulses, a first interface unit for receiving and converting said radio frequency data signals and said positional data signals into a format in which they can be recorded on tape by said video recorder; said first interface unit comprising means for generating modified line synchronising pulses, means for selecting a first group of said modified line synchronising pulses and transmitting said radio frequency data signals to the video recorder when said first group of modified line synchronising pulses occurs, and means for selecting a second different group of modified line synchronising pulses interleaved with said first group of modified line synchronising pulses and for transmitting said positional data signals to the video recorder when said second group of modified line synchronising pulses occurs, whereby said radio frequency ultrasonic data signals and said positional data signals are interleaved on the tape.

4. Apparatus as claimed in claim 3, in which said means for selecting the first group comprises a trigger pulse generator.

5. Apparatus as claimed in claim 3, in which said means for selecting the second group comprises a shift register and control logic therefor.

6. Apparatus as claimed in claim 3, further comprising a second interface unit for replaying the stored data signals, comprising a first display for the radio frequency signals and a second display for the positional signals and control means for the displays to activate one of said displays according to whether radio frequency or positional data is being replayed.

7. Apparatus as claimed in claim 6, in which the control means for the displays comprises a trigger pulse generator for controlling said first display and shift registers and a latch for controlling said second display.

* * * * *